(12) United States Patent
Muroguchi et al.

(10) Patent No.: US 8,308,925 B2
(45) Date of Patent: Nov. 13, 2012

(54) GAS SENSOR, CONTROL DEVICE THEREOF AND METHOD OF MEASURING NOX CONCENTRATION

(75) Inventors: Akihiro Muroguchi, Aichi (JP); San Jae Lee, Aichi (JP); Kenshin Kitoh, Aichi (JP)

(73) Assignee: NGK Insulators, Ltd., Nagoya (JP)

( * ) Notice: Subject to any disclaimer, the term of this patent is extended or adjusted under 35 U.S.C. 154(b) by 674 days.

(21) Appl. No.: 12/412,611

(22) Filed: Mar. 27, 2009

(65) Prior Publication Data

US 2009/0242427 A1   Oct. 1, 2009

(30) Foreign Application Priority Data

Mar. 31, 2008  (JP) ................. 2008-090078

(51) Int. Cl.
*G01N 27/406* (2006.01)
(52) U.S. Cl. ...... 204/424; 73/23.31; 73/23.32; 204/426; 204/427; 205/780.5; 205/781
(58) Field of Classification Search .......... 204/421–429; 205/780.5, 781, 782, 783
See application file for complete search history.

(56) References Cited

U.S. PATENT DOCUMENTS

| 5,672,811 | A | 9/1997 | Kato et al. |
|---|---|---|---|
| 6,036,841 | A | 3/2000 | Kato et al. |
| 2002/0017467 | A1* | 2/2002 | Ando et al. ............. 205/781 |

FOREIGN PATENT DOCUMENTS

| EP | 0 678 740 A1 | 10/1995 |
|---|---|---|
| EP | 1 087 226 A2 | 3/2001 |
| EP | 1 202 048 A2 | 5/2002 |
| EP | 1 995 588 A1 | 11/2008 |
| JP | 08-271476 A1 | 10/1996 |
| JP | 10-038845 A1 | 2/1998 |
| JP | 2004-037473 A1 | 2/2004 |
| WO | 2007/119311 A1 | 10/2007 |

* cited by examiner

*Primary Examiner* — Keith Hendricks
*Assistant Examiner* — Bach Dinh
(74) *Attorney, Agent, or Firm* — Burr & Brown

(57) ABSTRACT

A gas sensor for measuring NOx concentration in measurement gas based on sensor output depending on an amount of the detected oxygen includes an oxygen concentration control part for controlling oxygen concentration in the measurement gas. The oxygen concentration control part allows a control of oxygen concentration in the measurement gas to set at a designated value even after being mounted on an automobile, so that dependency of the sensor output with respect to oxygen concentration can be quantitatively detected. The sensor output for detecting NOx concentration is corrected by estimating an amount of a change accompanying the sensitivity degradation of the sensor output with respect to NOx concentration on the basis of a difference between oxygen output characteristics of the sensor output of an actually-used sensor and oxygen output characteristics of a sensor in the initial state, and correcting the sensor output in accordance with the amount of the change.

8 Claims, 7 Drawing Sheets

GAS SENSOR, CONTROL DEVICE THEREOF AND METHOD OF MEASURING NOX CONCENTRATION

BACKGROUND OF THE INVENTION

1. Field of the Invention

The present invention relates to a gas sensor for performing a correction of sensor output depending on concentration of a predetermined gas component in a measurement gas, a control device thereof and also relates to a method of measuring a NOx concentration.

2. Description of the Background Art

Conventionally, various measuring devices have been used for finding out concentration of a desired gas component in a measurement gas. A known device of measuring NOx concentration in a measurement gas such as a combustion gas, for example, is a gas sensor having a Pt-containing electrode and a Rh-containing electrode formed on an oxygen ion conductive solid electrolyte, such as zirconia ($ZrO_2$) (see Japanese Patent Application Laid-Open No. 8-271476 and Japanese Patent Application Laid-Open No. 2004-37473, for example).

In a gas sensor according to the above, concentration of a predetermined gas component is measured by detecting a current which flows at an electrode (measuring electrode) of a sensor element used for such detecting depending on the concentration of the predetermined gas component or the like, as sensor output.

Some of the gas sensors according to the above have a protection film consisted of a porous body and formed on a measuring electrode used for detection of a predetermined gas component for protecting it (see Japanese Patent Application Laid-Open No. 10-38845, for example).

In the case an internal combustion is driven with a gas sensor disclosed in Japanese Patent Application Laid-Open No. 8-271476, Japanese Patent Application Laid-Open No. 2004-37473 and Japanese Patent Application Laid-Open No. 10-38845 mounted on an emission system of the internal combustion in an automobile engine or the like (in an actual use of the gas sensor), substances such as Na, Mg, Ca or the like included in exhaust gas sometimes dissolve to a water vapor, for example, thereafter to enter into a sensor element through a gas inlet provided for introducing air.

As disclosed in Japanese Patent Application Laid-Open No. 10-38845, for a gas sensor where a protection film of a porous body is formed on a measuring electrode for protecting it, substances such as Na, Mg, Ca or the like after entering into the sensor element sometimes cause a clogging of this protection film consisted of the porous body (hereinafter, substances such as Na, Mg, Ca or the like causing such clogging are also referred to as contaminants). Such a clogging gradually proceeds with the actual use of the gas sensor.

The clogging of the protection film of the measuring electrode caused by contaminants such as Na, Mg, Ca or the like is a main factor of sensitivity degradation of a gas sensor to a predetermined gas component which is a target of measurement (i.e. a sensitivity change of sensor output). Also, such sensitivity degradation of the gas sensor leads to deterioration of measurement accuracy.

When a predetermined gas component targeted for measurement is NOx, in order to adapt to the above sensitivity degradation, it is possible to correct a change of the sensor output caused by sensitivity degradation, by means of associating NOx concentration with the sensor output after sensitivity degradation. It is implemented by investigating the relation between NOx concentration and the sensor output with actual measurement for a previously prepared gas including a NOx component of given concentration by the gas sensor after sensitivity degradation.

On the other hand, when an internal combustion is driven with a gas sensor mounted on an emission system of the internal combustion in an automobile engine or the like (in the actual use of the gas sensor), it is not so easy to prepare a gas including NOx of a predetermined concentration in the emission system. Accordingly, in such situation, it is difficult to correct the sensor output by a method of measuring the sensor output with respect to a gas including NOx of given concentration after sensitivity degradation to associate them with each other.

From the above, the sensitivity degradation of the gas sensor mainly caused by the clogging of the protection film of the measuring electrode caused due to the actual use of the gas sensor is one of the factors to deteriorate measurement accuracy of the gas sensor. It is, therefore, necessary to suppress deterioration of measurement accuracy by the sensitivity degradation of the gas sensor. Further, it is necessary to correct the sensor output with stable precision to adapt to the sensitivity degradation of the gas sensor and to maintain high measurement accuracy, under a situation in which a predetermined gas component targeted for measurement cannot be prepared at a desired concentration.

SUMMARY OF THE INVENTION

The present invention relates to a gas sensor for performing a correction of sensor output depending on concentration of a predetermined gas component in a measurement gas, a control device thereof and also relates to a method of measuring NOx concentration.

According to the present invention, a gas sensor for measuring NOx concentration in a measurement gas includes: (a) a sensor element having an oxygen control part for controlling oxygen concentration in the measurement gas, and a measuring part for measuring NOx concentration by detecting an amount of oxygen in the measurement gas while generating oxygen by resolving NOx in the measurement gas after being passed through the oxygen control part; and (b) a control device for controlling the sensor element having a detection element for detecting current oxygen output characteristics in the sensor element, and a correction element for correcting sensor output with respect to detection of NOx in the measurement gas in accordance with a difference between initial oxygen output characteristics and current oxygen output characteristics in the sensor element, wherein the oxygen output characteristics are characteristics of sensor output with respect to oxygen concentration.

Accordingly, how the oxygen output characteristics of the sensor output has been changed from its initial state can be detected by the oxygen control part of the sensor element, with the sensor being mounted on an object of such as an automobile. Thus, a change of dependency to NOx concentration with respect to the sensor element even after sensitivity degradation begins can be estimated by analogy with a change of the oxygen output characteristics so that it is possible to perform a measurement with high accuracy, compensating deterioration of accuracy of a gas sensor after sensitivity degradation.

Preferably, the correction element corrects a change rate Q of sensor output with respect to a change of NOx concentration on the basis of a change rate P and a change rate P0, the change rate P being a change rate of a sensor output with respect to a change of oxygen concentration and representing the current oxygen output characteristics, and the change rate P0 being a change rate of a sensor output with respect to a change of oxygen concentration and representing the initial oxygen output characteristics.

A change rate of a sensor output of a gas sensor with respect to NOx concentration before and after sensitivity degradation is regarded as being substantially coincident with a change rate of a sensor output of the gas sensor with respect to oxygen concentration before and after sensitivity degradation to correct a sensor output of the gas sensor after sensitivity degradation, thereby suppressing deterioration of measurement accuracy caused by the sensitivity degradation of the gas sensor.

It is therefore an object of the present invention to provide a gas sensor, a control device thereof and a method of measuring NOx concentration for being capable of compensating deterioration of measurement accuracy by correcting a change of a sensor output caused by the sensitivity degradation of the gas sensor.

DESCRIPTION OF THE INVENTION

<Configuration of Gas Sensor>

Figure 1:
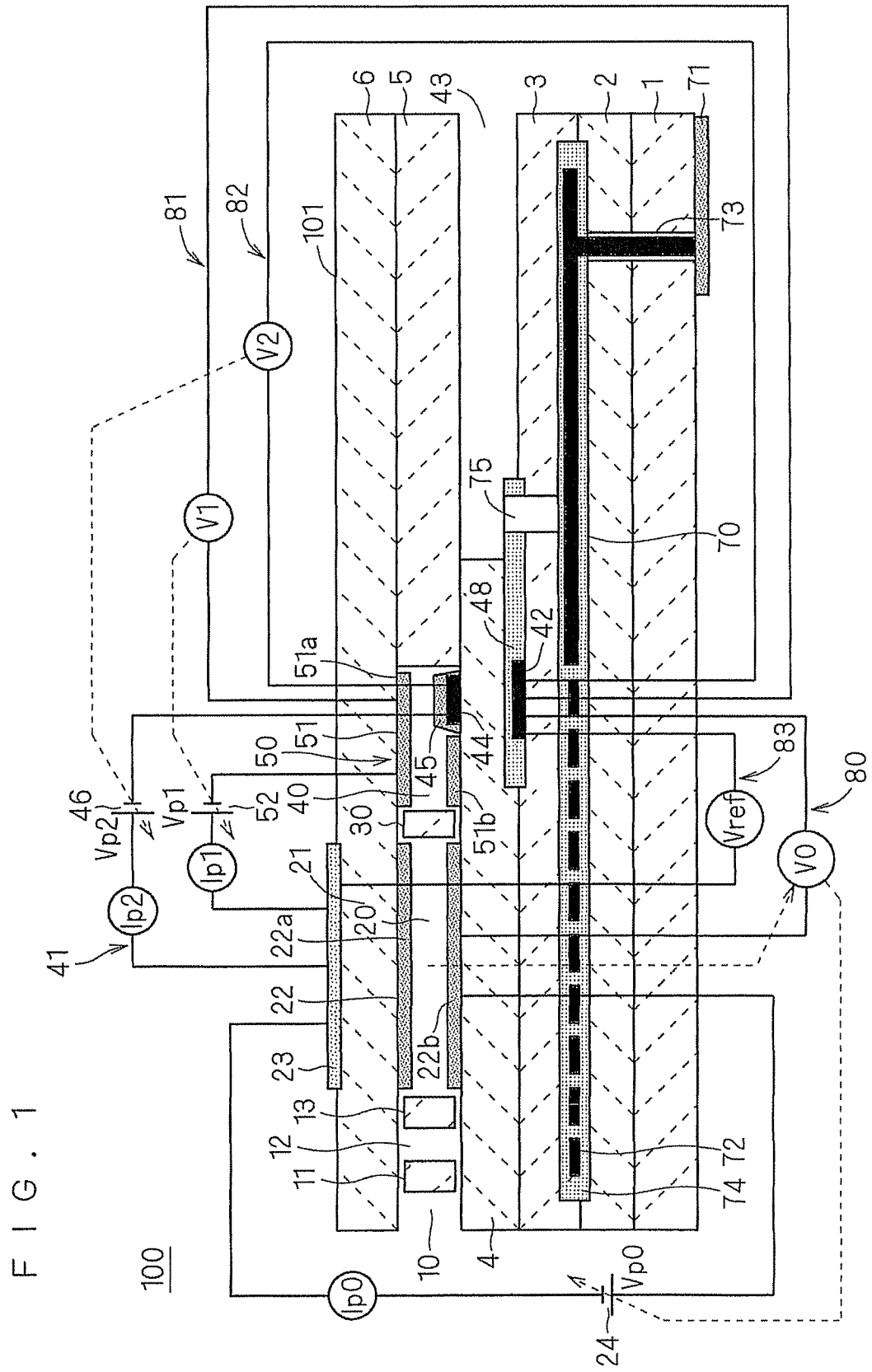
FIG. 1 is an outline sectional schematic view for showing a configuration of a gas sensor 100.

FIG. 1 is an outline sectional schematic view for showing one example of a configuration of a gas sensor 100 according to a preferred embodiment of the invention. The gas sensor 100 detects a predetermined gas component (NOx, $O_2$ or the like) in a gas (a measurement gas) which is an object of a measurement, and further, measures concentration thereof. The present embodiment will be described talking an example where the gas sensor 100 is a NOx sensor detecting nitrogen oxide (NOx) as a detection object component. The gas sensor 100 includes a sensor element 101 used for detection of a predetermined gas component in the measurement gas.

Figure 2:
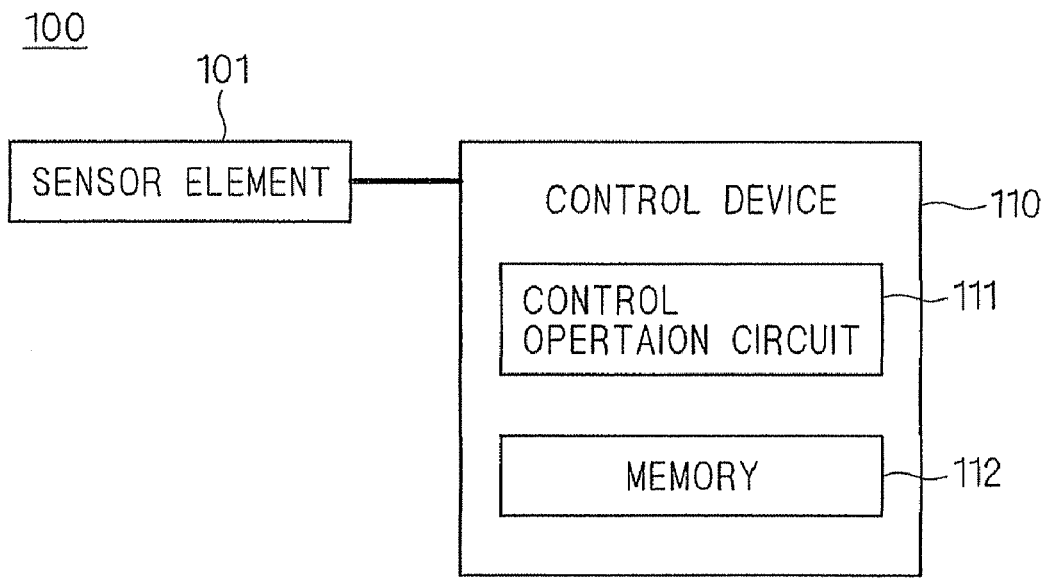
FIG. 2 is a view for showing a linkage of a sensor element and a control device in the gas sensor 100.

As shown in FIG. 2, the gas sensor 100 includes a control device 110 for controlling the sensor element 101 and generating a sensor output from an output current of the sensor element 101. The control device 110 includes a control operation circuit 111 composed of a microcomputer or the like and a memory 112 for storing various data. A correction of a sensor output as well as a control and current detection described below are implemented in the control operation circuit 111. Among elements in FIG. 1, a circuit system other than the sensor element 101 is an element of the control device 110.

The sensor element 101 shown in FIG. 1 is an elongated long plate-like element including a structure in which a first substrate layer 1, a second substrate layer 2, a third substrate layer 3, a first solid electrolyte layer 4, a spacer layer 5, and a second solid electrolyte layer 6 are laminated in this order from a bottom seen in FIG. 1, each of the layers being consisted of an oxygen ion conductive solid electrolyte. Also, the solid electrolyte consisting those six layers is dense and gastight. The sensor element 101 is manufactured by performing a predetermined processing and a printing of a circuit pattern on ceramics green sheets corresponding to each layer, laminating them, and further burning them to integrate, for example.

A gas inlet 10, a first diffusion control part 11, a buffer space 12, a second diffusion control part 13, a first internal space 20, a third diffusion control part 30 and a second internal space 40 are adjacently formed in this order to be in communication with one another between a lower surface of the second solid electrolyte layer 6 and an upper surface of the first solid electrolyte layer 4 at the end of the sensor element 101.

The gas inlet 10, the buffer space 12, the first internal space 20 and the second internal space 40 are provided by hollowing out the spacer layer 5, which is an internal space with an upper portion sectioned by the lower surface of the second solid electrolyte layer 6, a lower portion sectioned by the upper surface of the first solid electrolyte layer 4, and a side portion sectioned by a side surface of the spacer layer 5.

Each of the first diffusion control part 11, the second diffusion control part 13 and the third diffusion control part 30 is provided as two horizontally long slits (with an opening having a longitudinal direction in a direction perpendicular to Figure). A part from the gas inlet 10 to the second internal space 40 is also referred to as a gas distribution part.

A reference gas inlet space 43 is provided between an upper surface of the third substrate layer 3 and a lower surface of the spacer layer 5 with a side portion sectioned by a side surface of the first solid electrolyte layer 4, at a position which is far from the end than the gas distribution part is. For example, air is introduced to the reference gas inlet space 43 as a reference gas for measuring NOx concentration.

An air induction layer 48 is consisted of porous alumina and a reference gas is introduced to the air induction layer 48 through a reference gas inlet space 43. Further, the air induction layer 48 is formed to cover a reference electrode 42.

The reference electrode 42 is formed to be interposed between the upper surface of the third substrate layer 3 and the first solid electrolyte layer 4, and surrounded by the air induction layer 48 leading to the reference gas inlet space 43, as described above. As described later, it is possible to measure oxygen concentration (oxygen partial pressure) in the first internal space 20 and the second internal space 40 by the reference electrode 42.

The gas inlet 10 of the gas distribution part is a part which is open to an outside, and a measurement gas is brought into the sensor element 101 from the outside therethrough.

The first diffusion control part 11 provides a predetermined diffusion resistance to the measurement gas brought into from the gas inlet 10.

The buffer space 12 is a space provided for introducing the measurement gas introduced from the first diffusion control part 11 to the second diffusion control part 13.

The second diffusion control part 13 provides a predetermined diffusion resistance to the measurement gas introduced into the first internal space 20 from the buffer space 12.

When the measurement gas is introduced from the outside of the sensor element 101 into the first internal space 20, the measurement gas rapidly brought into the sensor element 101 from the gas inlet 10 due to pressure fluctuation (pulsation of exhaust pressure if a measurement gas is an emission gas of automobiles) of the measurement gas in the outside is not directly introduced to the first internal space 20, but is introduced into the first internal space 20 after concentration fluctuation of the measurement gas is counteracted through the first diffusion control part 11, the buffer space 12 and the second diffusion control part 13. Thereby, the concentration fluctuation of the measurement gas introduced into the first internal space can be mostly ignored.

The first internal space 20 is provided as a space for controlling oxygen partial pressure in the measurement gas introduced through the second diffusion control part 13. The oxygen partial pressure is controlled by operating a main pumping cell 21.

The main pumping cell 21 is an electrochemical pumping cell composed of an inside pump electrode 22 including a ceiling electrode part 22a provided on an almost whole surface in a part of the lower surface of the second solid electrolyte layer 6 facing the first internal space 20, an outside pump electrode 23 provided in a region corresponding to the ceiling electrode part 22a on an upper surface of the second solid electrolyte layer 6 to be exposed to the outside, and the second solid electrolyte layer 6 interposed between those electrodes.

The inside pump electrode 22 is formed over the solid electrolyte layers above and below (the second solid electrolyte layer 6 and the first solid electrolyte layer 4) sectioning the first internal space 20 and the spacer layer 5 providing a sidewall. More specifically, the ceiling electrode part 22a is formed on the lower surface of the second solid electrolyte layer 6 providing a ceiling surface of the first internal space 20, and a bottom electrode part 22b is formed on the upper surface of the first solid electrolyte layer 4 providing a bottom surface. Then, a side electrode part 22c (not shown) is formed on a sidewall surface (inner surface) of the spacer layer 5 composing both sidewalls of the first internal space 20 so as to connect the ceiling electrode part 22a to the bottom electrode part 22b. That is to say, the inside pump electrode 22 is disposed to make a tunnel-like structure at a position thereof.

The inside pump electrode 22 and the outside pump electrode 23 are formed as porous cermet electrodes (e.g. cermet electrodes consisted of Pt including Au of 1% and $ZrO_2$). Further, the inside pump electrode 22 being in contact with the measurement gas is formed using material in which reduction ability to an NO component in the measurement gas is weakened, or material without reduction ability.

The main pumping cell 21 is provided with a variable power source 24 outside the sensor element 101. The variable power source 24 applies a desired pump voltage Vp0 between the inside pump electrode 22 and the outside pump electrode 23 to flow a pump current Ip0 in a positive direction or a negative direction between the inside pump electrode 22 and the outside pump electrode 23, allowing to pump out oxygen in the first internal space 20 to the outside or to pump in oxygen in the outside into the first internal space 20.

An oxygen partial pressure detecting sensor cell for main pump control 80 which is an electrochemical sensor cell is composed of the inside pump electrode 22, the second solid electrolyte layer 6, the spacer layer 5, the first solid electrolyte layer 4, the third substrate layer 3 and the reference electrode 42 in order to detect oxygen concentration (oxygen partial pressure) in the atmosphere of the first internal space 20.

Oxygen concentration (oxygen partial pressure) in the first internal space 20 is obtained by measuring an electromotive force V0 on the oxygen partial pressure detecting sensor cell for main pump control 80. Further, the pump current Ip0 is controlled by feedback controlling the pump voltage Vp0 to set the electromotive force V0 to be constant, thereby allowing oxygen concentration in the first internal space 20 to maintain a predetermined constant value.

The third diffusion control part 30 provides a predetermined diffusion resistance to the measurement gas in which oxygen concentration (oxygen partial pressure) has been controlled in the first internal space 20 by operating the main pumping cell 21, and introduces the measurement gas into the second internal space 40.

The second internal space 40 is provided as a space for performing a process to measure concentration of nitrogen oxide (NOx) in the measurement gas introduced through the third diffusion control part 30. NOx concentration is measured by operating a measuring pumping cell 41 in the second internal space 40 where oxygen concentration is controlled in advance mainly by an auxiliary pumping cell 50.

Oxygen concentration (oxygen partial pressure) is previously controlled in the first internal space 20, and thereafter, oxygen partial pressure in the measurement gas introduced through the third diffusion control part 30 is further controlled in the second internal space 40 by the auxiliary pumping cell 50. Accordingly, oxygen concentration in the second internal space 40 can be maintained to be constant with high accuracy so that the gas sensor 100 can perform the measurement of a NOx concentration with high accuracy.

The auxiliary pumping cell 50 is an auxiliary electrochemical pumping cell composed of an auxiliary pump electrode 51 provided on a substantially whole surface in a part of the lower surface of the second solid electrolyte layer 6 facing the second internal space 40 and including a ceiling electrode part 51a, the outside pump electrode 23 (not limited to the outside pump electrode 23, but any appropriate electrode outside the sensor element 101 will do) and the second solid electrolyte layer 6.

The auxiliary pump electrode 51 is disposed in the second internal space 40 to make a tunnel-like structure similar to the inside pump electrode 22 provided in the preceding first internal space 20. Specifically, the tunnel-like structure is made by forming a ceiling electrode part 51a on the second solid electrolyte layer 6 providing a ceiling surface of the second internal space 40, forming a bottom electrode part 51b on the first solid electrolyte layer 4 providing a bottom surface of the second internal space 40, and forming a side electrode part 51c (not shown) on both side surfaces of the spacer layer 5 providing a sidewall of the second internal space 40 so as to connect the ceiling electrode part 51a to the bottom electrode part 51b.

Similarly to the inside pump electrode 22, the auxiliary pump electrode 51 is formed using material in which reduction ability to an NO component in the measurement gas is weakened, or material without reduction ability.

The auxiliary pumping cell 50 is provided with a variable power source 46 outside the sensor element 101. The variable power source 46 applies a desired voltage Vp1 between the auxiliary pump electrode 51 and the outside pump electrode 23 to pump out oxygen in the atmosphere of the second internal space 40 to the outside or to pump in oxygen in the outside into the second internal space 40.

An oxygen partial pressure detecting sensor cell for auxiliary pump control 81 which is an electrochemical sensor cell is composed of the auxiliary pump electrode 51, the reference electrode 42, the second solid electrolyte layer 6, the spacer layer 5, the first solid electrolyte layer 4 and the third substrate layer 3 in order to control oxygen partial pressure in the atmosphere of the second internal space 40.

The auxiliary pumping cell 50 performs a pumping with a variable power source 52 whose a voltage is controlled on the basis of an electromotive force V1 detected by the oxygen partial pressure detecting sensor cell for auxiliary pump control 81. As a result, oxygen partial pressure in the atmosphere of the second internal space 40 is controlled to be a lower partial pressure not substantially affecting measurement of NOx.

At the same time, its pump current Ip1 is used for controlling the electromotive force on the oxygen partial pressure detecting sensor cell for main pump control 80. Specifically, the pump current Ip1 is input to the oxygen partial pressure detecting sensor cell for main pump control 80 as a control signal, and is controlled by controlling the electromotive force V0 so that a gradient of oxygen partial pressure in the measurement gas introduced into the second internal space 40 from the third diffusion control part 30 is maintained constant. When the gas sensor 100 is used as a NOx sensor, oxygen concentration is maintained at a constant value of approximately 0.001 ppm in the second internal space 40 by operating the main pumping cell 21 and the auxiliary pumping cell 50.

The measuring pumping cell 41 assumes the measurement of NOx concentration in the measurement gas in the second internal space 40. The measuring pumping cell 41 is an electrochemical pumping cell composed of a measuring electrode 44 provided on the upper surface of the first solid electrolyte layer 4 facing the second internal space 40, spaced apart from the third diffusion control part 30, the outside pump electrode 23, the second solid electrolyte layer 6, the spacer layer 5 and the first solid electrolyte layer 4.

The measuring electrode 44 is a porous cermet electrode which is substantially oblong in a plane view. The measuring electrode 44 also serves as a NOx reduction catalyst for resolving NOx in the atmosphere of the second internal space 40. Moreover, the measuring electrode 44 is covered with a fourth diffusion control part 45.

The fourth diffusion control part 45 is a film composed of a porous body mainly consisted of alumina ($Al_2O_3$). The fourth diffusion control part 45 functions to limit the amount of NOx flowing into the measuring electrode 44 and also functions as a protection layer for the measuring electrode 44.

In the measuring pumping cell 41, oxygen generated by decomposition of nitrogen oxide in the atmosphere surrounding the measuring electrode 44 is pumped out and an amount of the generated oxygen can be detected as a pump current Ip2 (the pump current Ip2 is one of sensor output obtained in the gas sensor 100, and hereinafter, the current Ip2 generated by pumping out oxygen surrounding the measuring electrode 44 is also referred to as a sensor output Ip2).

An oxygen partial pressure detecting sensor cell for measuring pump control 82 which is an electrochemical sensor cell is composed of the second solid electrolyte layer 6, the spacer layer 5, the first solid electrolyte layer 4, the third substrate layer 3, the measuring electrode 44 and the reference electrode 42 in order to detect oxygen partial pressure surrounding the measuring electrode 44. The variable power source 46 is controlled on the basis of an electromotive force V2 detected by the oxygen partial pressure detecting sensor cell for measuring pump control 82.

The measurement gas introduced into the second internal space 40 reaches the measuring electrode 44 through the fourth diffusion control part 45 under a situation in which oxygen partial pressure is controlled. Nitrogen oxide in the measurement gas surrounding the measuring electrode 44 is reduced ($2NO \rightarrow N_2+O_2$) to generate oxygen. When the generated oxygen is pumped by the measuring pumping cell 41, the pump voltage Vp2 of the variable power source 46 is controlled so that the electromotive force V2 detected by the oxygen partial pressure detecting sensor cell for measuring pump control 82 is maintained constant. The amount of oxygen surrounding the measuring electrode 44 is proportional to concentration of nitrogen oxide in the measurement gas, so that concentration of nitrogen oxide in the measurement gas is calculated by using the pump current Ip2 in the measuring pumping cell 41.

If the measuring electrode 44, the first solid electrolyte layer 4 and the third substrate layer 3 are combined to compose an oxygen partial pressure detecting means as an electrochemical sensor cell, an electromotive force according to a difference between the amount of oxygen generated by reduction of a NOx component in the atmosphere surrounding the measuring electrode 44 and the amount of oxygen included in the reference air can be detected, thereby allowing to obtain concentration of a NOx component in the measurement gas.

An electrochemical sensor cell 83 is composed of the second solid electrolyte layer 6, the spacer layer 5, the first solid electrolyte layer 4, the third substrate layer 3, the outside pump electrode 23 and the reference electrode 42. An electromotive force Vref obtained by this sensor cell 83 allows oxygen partial pressure in the measurement gas outside the sensor to be detected.

The sensor element 101 includes a heater part 70 functioning to control temperature to heat the sensor element and keep it warm in order to enhance oxygen ion conductivity of solid electrolyte. The heater part 70 includes a heater electrode 71, a heater 72, a through hole 73, a heater insulating layer 74 and a pressure diffusion hole 75.

The heater electrode 71 is formed to make contact with the lower layer of the first substrate layer 1. The heater part 70 can be fed by outside by connecting the heater electrode 71 to the outside power source.

The heater 72 is an electrical resistor formed to be interposed between the second substrate layer 2 and the third substrate layer 3 from above and below. The heater 72 is connected to the heater electrode 71 via the through hole 73, and generates heat by feeding from outside through the heater electrode 71 to heat solid electrolyte composing a solid electrolyte layer and keep it warm.

The heater 72 is buried over the whole area from the first internal space 20 to the second internal space 40 so that the entire sensor element 101 can be heated and kept warm at a temperature activating the above solid electrolyte.

The heater insulating layer 74 consisted of an insulator such as alumina is formed on an upper surface and a lower surface of the heater 72 in order to obtain electronic insulation among the second substrate layer 2, the third substrate layer 3 and the heater 72, that is, to obtain the electronic insulation among each electrode of the sensor element 101 and the heater 72.

The pressure dissipation hole 75 is formed to penetrate the third substrate layer 3, being in communication with the reference gas inlet space 43 and allowing to reduce rise of inner pressure in the heater insulating layer 74 accompanied by a temperature rise.

In the gas sensor 100 having the above-described structure, the measurement gas is provided to the measuring pumping cell 41, with oxygen partial pressure constantly maintained at a fixed low value (a value substantially not affecting the measurement of NOx) by operating the main pumping cell 21 and the auxiliary pumping cell 50. Accordingly, the pump current Ip2 flowing by pumping out oxygen generated by reducing NOx is to be proportional to the reduced NOx concentration, and NOx concentration in the measurement gas is found out based thereon.

<Sensitivity Degradation of Gas Sensor and Correction of Sensor Output>

When the gas sensor 100 is continued to be actually used as a gas sensor, being mounted on an emission system of an internal combustion of an automobile engine or the like, the sensitivity of the gas sensor 100 to a gas component targeted for measurement is gradually lowered. That is, the sensor output of the gas sensor 100 is changed. Degradation of the sensor output of the gas sensor 100 in the above leads to deterioration of the measurement accuracy of the gas sensor 100.

Figure 3:
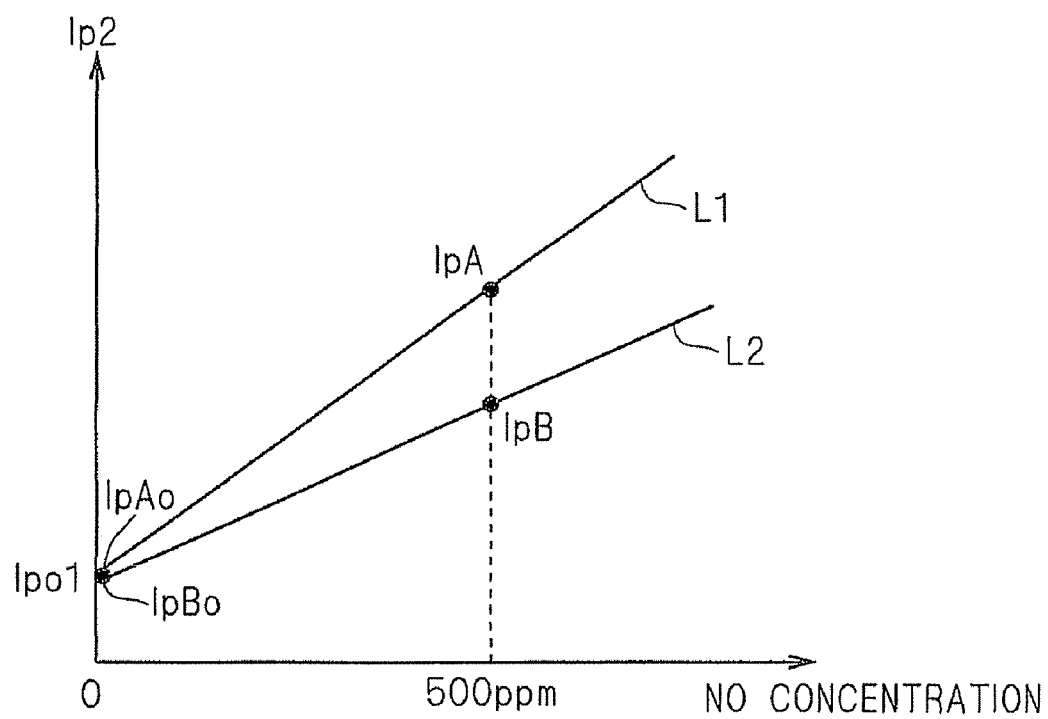
FIG. 3 is a view for schematically showing a change of a relation between NO concentration and a current Ip2 due to sensitivity degradation.

FIG. 3 is a view for schematically showing an example of sensitivity degradation of the gas sensor 100. FIG. 3 shows the relation of the sensor output Ip2 and NO concentration in the gas sensor 100 without the sensitivity degradation, and the relation of the sensor output Ip2 and NO concentration in the gas sensor 100 after the sensitivity degradation.

In FIG. 3, a characteristics line L1 shows the relation of the sensor output Ip2 and NOx concentration in the gas sensor 100 without the sensitivity degradation. The sensor output Ip2 when NO concentration is 500 ppm is shown as IpA.

When the gas sensor 100 is manufactured, NOx of given concentration is measured to detect the sensor output Ip2 at that time. Thereby, NOx concentration and the sensor output Ip2 are associated with each other. The gas sensor 100 at this state where the association is accurate like that is defined to the gas sensor 100 without the sensitivity degradation. For instance, the gas sensor 100 shipped as a product can be said to be the gas sensor 100 without the sensitivity degradation.

In order to associate the sensor output Ip2 with NOx concentration, for example, with respect to the gas sensor 100 without sensitivity degradation shown by the characteristics line L1 in FIG. 3, each value of the sensor output Ip2 when NO concentration is 500 ppm and the sensor output Ip2 when NO concentration is 0 ppm is measured. Further, NO concentration and the sensor output Ip2 are associated with each other by using NO concentration being proportional to the sensor output Ip2. NO concentration to be measured is not limited to two kinds of 0 ppm and 500 ppm in this association. The magnitude of the sensor output Ip2 depends on the amount of oxygen adjacent to the measuring electrode 44. This amount of oxygen depends on the amount of oxygen generated by decomposition of NOx. This is why there is the proportional relation between NOx concentration and the sensor output Ip2.

A characteristics line L2 shows the relation of NOx concentration and the sensor output Ip2 in the gas sensor 100 after sensitivity degradation. The sensor output Ip2 when NO concentration is 500 ppm is shown as IpB, and the sensor output Ip2 when NO concentration is 0 ppm is shown as IpBo.

The gas sensor 100 after sensitivity degradation refers to the gas sensor 100 where in actually measuring concentration of a predetermined gas (NOx) in the measurement gas under the actual use situation, the proportional relation between NOx concentration or oxygen concentration and the sensor output Ip2 is not considerably lost, even with the sensitivity of a gas sensor being lowered due to contaminants clogging in the fourth diffusion control part 45.

The values of IpAo and IpBo which are values of the sensor output Ip2 of the characteristics lines L1 and L2 when NO concentration is 0 ppm are almost equivalent to each other so that the values of IpAo and IpBo may be set to be identical to each other by obtaining the average value Ipo1 therebetween. When NO concentration is 0 ppm, a small amount of the pump current Ip2 is going to flow.

As shown in FIG. 3, the pump current Ip2 (sensor output Ip2) flowing in the measuring pumping cell 41 of the gas sensor 100 after sensitivity degradation, indicated in the characteristics line L2, becomes lower than that of the initial gas sensor 100, indicated in the characteristics line L1. This lowering means the degradation of the sensitivity of the gas sensor 100.

There are several reasons to cause sensitivity degradation of a gas sensor, but one of main causes is that contaminants, such as Na, Mg, Ca or the like included in an emission gas caused by driving the internal combustion of an engine or the like, enter into the sensor element 101, and make a clogging in the fourth diffusion control part 45 which is a protection film formed of a porous body for protecting the measuring electrode 44, as described above.

When a predetermined gas component targeted for measurement is NOx or the like, in order to adapt to the above sensitivity degradation, it is possible to correct a change of the sensor output due to the sensitivity degradation, by means of associating NOx concentration with the sensor output after the sensitivity degradation. It is implemented by investigating the relation of NOx concentration and the sensor output with actual measurement for a previously prepared gas including a NOx component of given concentration by a gas sensor after the sensitivity degradation.

When an internal combustion is driven with a gas sensor mounted on an emission system of the internal combustion in an automobile engine or the like (in an actual use of the gas sensor), it is not so easy to prepare a gas including NOx of a predetermined concentration in the emission system of the automobile engine. Accordingly, in such situation, it is difficult to correct the sensor output by a method of measuring the sensor output after the sensitivity degradation with respect to a gas including NOx of given concentration to associate them with each other.

In contrast, the gas sensor 100 allows to measure and control oxygen concentration with high accuracy by operating the main pumping cell 21 in the first internal space 20 and the auxiliary pumping cell 50 in the second internal space 40. Actually, oxygen concentration can be controlled in the gas sensor 100 without substantially any affection from the sensitivity degradation.

In the present invention, a value of the sensor output Ip2 measured after the sensitivity degradation is corrected by using the property of the gas sensor 100 that it is capable of controlling oxygen concentration with high accuracy. Therefore, a correction in the present invention could be applied even while driving by changing a controlling method at a side of a circuit as well as at the time of stopping of a car (e.g., at the time of checking a car).

Hereinafter, a correction method for a change of the sensor output due to the sensitivity degradation of the gas sensor 100, specifically, a method of correcting the change of the sensor output due to the sensitivity degradation of a sensor caused by contaminants clogging in the fourth diffusion control part 45 will be described in detail.

<First Correction Method>

Next, a first correction method for correcting a change of a sensor output due to sensitivity degradation caused by a clogging of a porous body forming the fourth diffusion control part 45 with the use of the gas sensor 100 will be described. In the first correction method, the sensor output Ip2 in measuring NOx with the gas sensor 100 after degradation is corrected on the basis of the relation of oxygen concentration and the sensor output before and after the degradation of the gas sensor 100.

When measuring NOx concentration, the sensor output Ip2 derives from $O_2$ generated by a reduction reaction expressed by the following formula: $2NO \rightarrow N_2 + O_2$ occurring on the measuring electrode 44. It is similar to the measurement of oxygen concentration in that the sensor output Ip2 derives from $O_2$. Thus, these both sensor outputs Ip2 are to be similarly affected by diffusion resistance in the fourth diffusion control part 45. Therefore, in between the initial gas sensor 100 and the gas sensor 100 after sensitivity degradation, a change rate of the sensor output Ip2 when measuring oxygen concentration can be said to be almost same as a change rate of the sensor output Ip2 deriving from $O_2$ generated by reduction expressed by the following formula: $2NO \rightarrow N_2 + O_2$ when measuring NOx.

Using such things, a change of the sensor output Ip2 by NOx measurement is calculated from a change of the sensor output Ip2 by $O_2$ measurement, and then a correction is performed to obtain a value to be originally measured (a value of the sensor output Ip2 to be obtained if the gas sensor is in its initial state).

Figure 4:
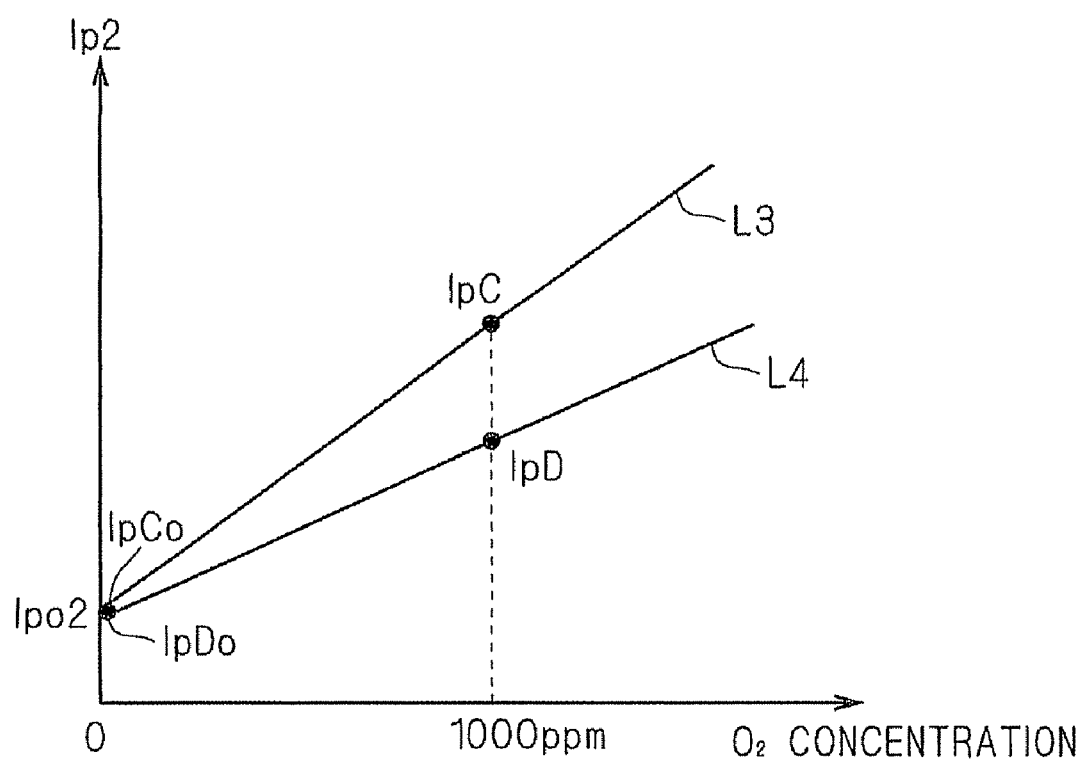
FIG. 4 is a view for schematically showing a relation of oxygen concentration and the current Ip2 in an initial gas sensor 100 and an actually-used gas sensor 100 after the sensitivity degradation.

The relation of the gas sensor 100 before and after the sensitivity degradation and the sensor output Ip2 will be described. FIG. 4 is a view for schematically showing the relation of oxygen concentration and the sensor output Ip2 in the gas sensor 100 without the sensitivity degradation and the gas sensor 100 after the sensitivity degradation. In FIG. 4, a characteristics line L3 shows the relation of oxygen concentration and the sensor output Ip2 in the gas sensor 100 without the sensitivity degradation. The sensor output Ip2 when oxygen concentration is 1000 ppm is shown as IpC, and the sensor output Ip2 when oxygen concentration is 0 ppm is shown as IpCo. In FIG. 4, a characteristics line L4 shows the relation of oxygen concentration and the sensor output Ip2 in the gas sensor 100 after the sensitivity degradation. The sensor output Ip2 when oxygen concentration is 1000 ppm is shown as IpD, and the sensor output Ip2 when oxygen concentration is 0 ppm is shown as IpDo.

The values on the characteristics lines L3 and L4 when oxygen concentration is 0 ppm are almost equivalent to each other so that the sensor output values of IpCo and IpDo may be replaced by an identical value of Ipo2 obtained by averaging the sensor output values of IpCo and IpDo.

In FIG. 4, the value of the sensor output Ip2 in the characteristics line L4 after the sensitivity degradation is lowered compared to the characteristics line L3 showing the sensor output Ip2 of the gas sensor 100 without the sensitivity degradation. This lowering means the degradation of the sensitivity of the sensor output Ip2 to oxygen concentration.

Hereinafter, the specific correction method will be described, but the terms below are used as follows.

(1) An "initial sensor" (a sensor in an initial state) is the gas sensor 100 before use for measuring NOx or the gas sensor 100 at beginning of use, but in which any degradation hardly proceeds, and representatively, it is the gas sensor 100 before being shipped.

(2) An "actually-used sensor" is the gas sensor 100 actually used and is in a state in which sensitivity degradation is caused by repeating a NOx measurement (or in a state in which sensitivity degradation is just occurring). It corresponds to a gas sensor actually mounted on an automobile or the like, and the gas sensor 100 in the above state is an actual target of a correction.

(3) A "reference sensor" has the same configuration as the gas sensor 100 which is the target of a correction, but is a different sensor from the target of a correction, which is not used in "the first correction method", but used in "a second correction method".

Figure 5:
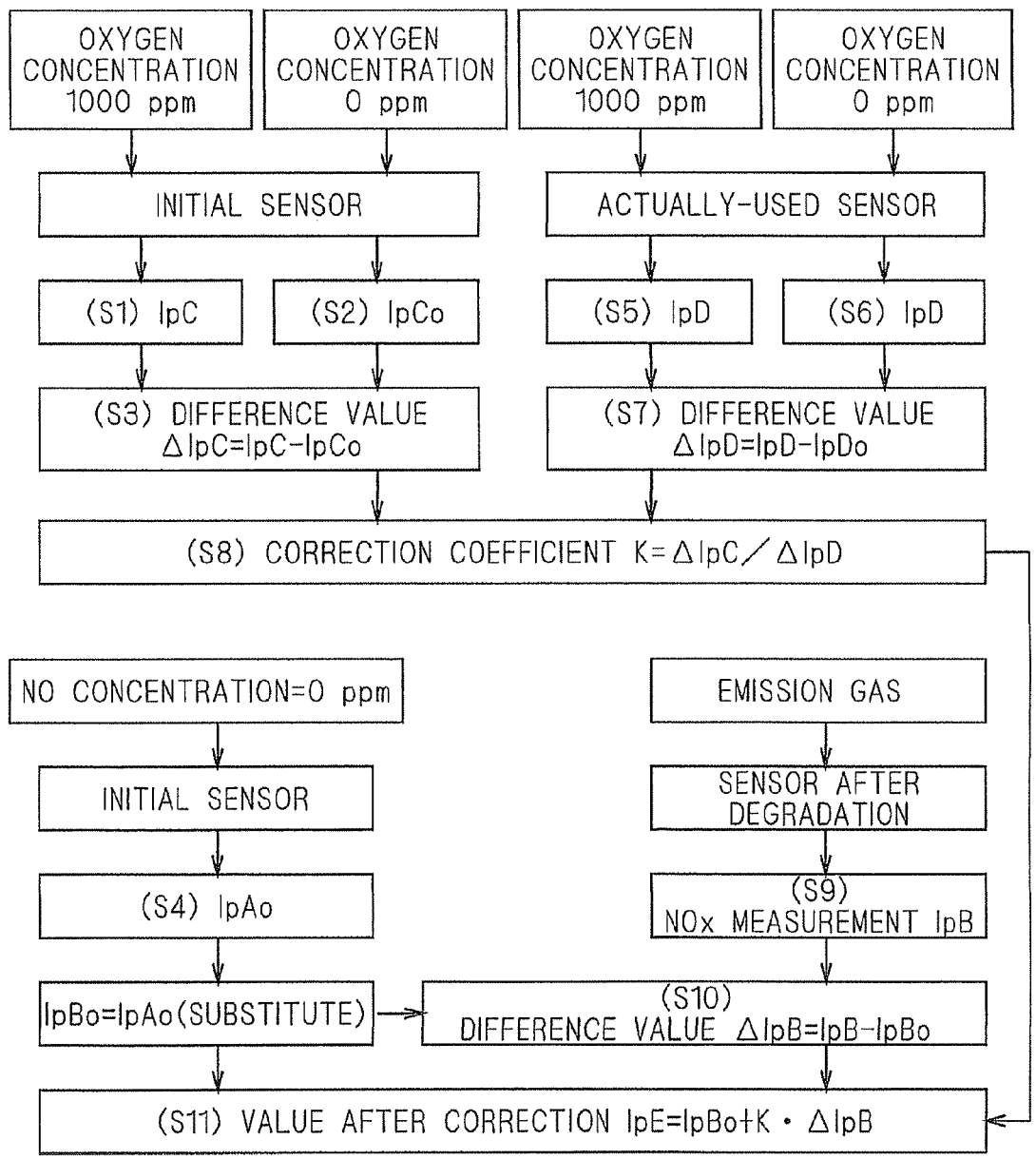
FIG. 5 is a view for showing a flow of a first correction method.

FIG. 5 shows the content of a first correction method in relation to a data flow. The reference numeral of each step is applied in parenthesis.

First, the initial sensor is used for detecting the sensor output Ip2 under the condition that oxygen concentration is 1000 ppm in the second internal space 40 (step S1). A value of the current Ip2 at this time is represented by IpC.

Oxygen concentration at that time is not necessarily limited to 1000 ppm, but it is preferable that it falls within a range where NOx is not decomposed by the measuring electrode 44 (a range approximately from 0.01 ppm to 10000 ppm), since the measurement gas sometimes includes NOx under the situation where the gas sensor 100 is actually used. So, an environment where only oxygen derived from oxygen molecule is generated in the oxygen component of the measurement gas is prepared, without virtually generating an oxygen component derived from NOx. As described above, in the gas sensor 100, oxygen concentration in the above range is obtained by controlling with high accuracy by operating two pumping cells of the main pumping cell 21 in the first internal space 20 and the auxiliary pumping cell 50 in the second internal space 40.

The first correction method will be described with an example where a voltage of 400 mV is applied between the measuring electrode 44 and the outside pump electrode 23.

Next, the sensor output Ip2 under the condition that oxygen concentration in the second internal space 40 is 0 ppm is detected by the initial sensor (step S2). A value of the sensor output Ip2 at this time is represented by IpCo. Also, a difference value is calculated by the following equation (step S3).

$$\Delta IpC = IpC - IpCo \quad (1)$$

In the above, a difference of oxygen concentration at two measurement values is 1000 ppm and 0 ppm. Thus, the relation of the change rate P0 as initial oxygen output characteristics and the above difference value $\Delta IpC$ is represented by the following equation.

$$P0 = \Delta IpC / 1000 \quad (2)$$

Therefore, the change rate P0 is obtained substantively by a linear approximation.

Next, an output value IpAo of the initial sensor under the condition that NO concentration is 0 ppm is detected (step S4). As shown in FIG. 3, this output value IpAo is substantially same as the output value IpBo of the actually-used sensor when NO concentration is 0 ppm. The output value IpAo of the initial sensor is later used as the substitute for the output value IpBo of the actually-used sensor in this example.

The above steps are performed before shipping the gas sensor 100 or mounting it on an automobile, and then each obtained value is stored in the memory 112 in the control device 110 of the gas sensor 100.

The measurement and calculation described below are performed for the gas sensor 100 (actually-used sensor) used for measuring NOx with being mounted on the automobile, and implemented as a control operation of the control device 110. First, a current value IpD of the actually-used sensor, which is the sensor output Ip2 with oxygen concentration of 1000 ppm, is detected (step S5). That is, oxygen concentration at this detection is same as the concentration at the time of measurement of the above initial sensor, which is exemplified by that oxygen concentration in the second internal space 40 is 1000 ppm. Also, a voltage applied between the measuring electrode 44 and the outside pump electrode 23 is 400 mV. A value of the sensor output Ip2 at this time is represented by IpD.

Further, the current value Ip2 under the condition that oxygen concentration is 0 ppm is detected in the actually-used sensor (step S6). A value of the current Ip2 at this time is represented by IpDo. Also, a difference value is calculated by the following equation and stored in the memory 112 (step S7).

$$\Delta IpD=IpD-IpDo \quad (3)$$

In the above, a difference of oxygen concentration at two measurement values is 1000 ppm and 0 ppm. Thus, the relation of the change rate P as oxygen output characteristics of the actually-used sensor and the above difference value $\Delta IpD$ is represented by the following equation.

$$P=\Delta IpD/1000 \quad (4)$$

Therefore, the change rate P is obtained substantively by a linear approximation.

Next, a correction coefficient K is calculated by the following equation (step S8).

$$K=\Delta IpC/\Delta IpD=(IpC-IpCo)/(IpD-IpDo) \quad (5)$$

A value of the correction coefficient K is also stored in the memory 112 in the control device 110 of the gas sensor 100.

Preparation of an Output Correction is Completed Up to Here, and a Correction process is performed hereinafter in synchronization with an operation of the actually-used sensor for performing a normal measurement of an emission gas. Accordingly, the operation hereinafter is performed not only once, but repeated in a short time for each NOx measurement cycle for the emission gas under a control of the control device 110.

NO concentration for the emission gas with the actually-used sensor is measured to obtain its output value IpB (a step S9).

Then, a difference value corresponding to an elevated value from the output value IpBo (=IpAo) for the actually-used sensor when NOx concentration is 0 ppm is calculated by the following equation (step S10).

$$\Delta IpB=IpB-IpBo \quad (6)$$

Accordingly, this difference value is amplified by the correction coefficient K, and added with the reference output value IpBo (=IpAo). As a result, an output value of the actually-used sensor in a NOx measurement is corrected with the calculation of the following equation (step S11).

$$IpE=IpBo+K\cdot\Delta IpB \quad (7)$$

When a change rate of a sensor output before the correction to a change rate of NOx concentration is represented by Q, and a change rate of a sensor output after the correction is Qc, letting actual NOx concentration at that time be Dnox, from the above correction equations, the following equations are established.

$$Q=\Delta IpB/Dnox \quad (8)$$

$$Qc=K\cdot\Delta IpB/Dnox \quad (9)$$

Thus, as for the relation of the change rate, the following equation is established from those above equations and the equations (2) and (4).

$$Qc=(P/P0)\cdot Q \quad (10)$$

When output characteristics with respect to the initial sensor is applied to the sensor output Q before the correction, the following equation is established.

$$Q=Q0 \quad (11)$$

Thus, the equation (10) is expressed as follows.

$$Qc=(P/P0)\cdot Q0 \quad (12)$$

A measuring signal in accordance with the current value IpE after the correction is output to a control device (ECU) of an engine as a current (corrected) measurement value of NOx concentration.

As described above, the correction coefficient K is obtained by the relation of oxygen concentration and the sensor output in the initial sensor and actually-used sensor (a changing state of oxygen measurement characteristics), and a correction value $\Delta IpE=K\cdot\Delta IpB$ is calculated by the correction coefficient K with respect to the NOx measurement output of the actually-used sensor, thereby allowing to calculate the output value IpE of the actually-used sensor after the correction by the correction value $\Delta IpE$.

Figure 6:
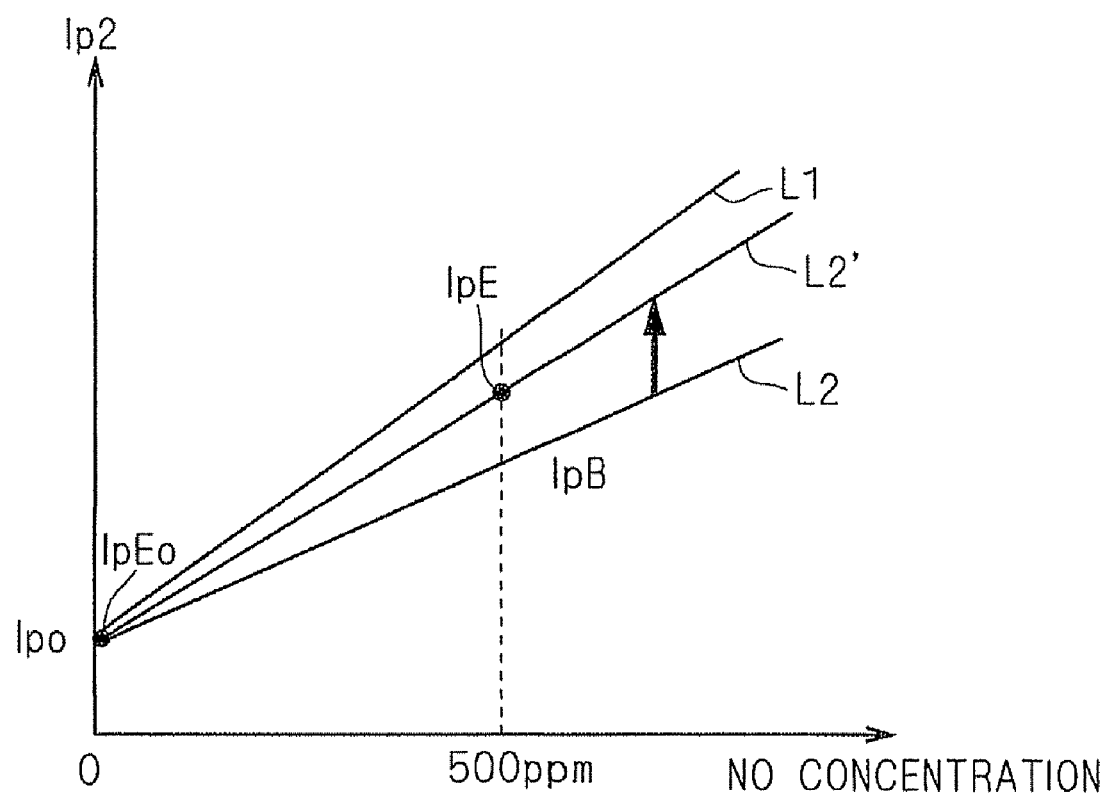
FIG. 6 is a view for schematically showing a relation of NO concentration and the current Ip2 in the initial gas sensor 100, the actually-used gas sensor 100 after the sensitivity degradation and a gas sensor 100 after a correction of a sensor output.

FIG. 6 is a view for schematically showing measurement characteristics of NO concentration in the initial sensor and the actually-used sensor before and after the correction. The characteristics lines L1 and L2 are same as those shown in FIG. 3. The characteristics line L1 shows the relation of NOx concentration and the sensor output Ip2 in the initial sensor, and the characteristics line L2 shows the relation of NOx concentration and the sensor output Ip2 in the actually-used sensor (before the correction). The characteristics line L2' shows the sensor output Ip2 obtained by correcting an output of the actually-used sensor with the above correction coefficient K.

The characteristics line L2' is considerably drawing closer to the characteristics line L1 than the characteristics line L2. Those lines are not completely coincident with each other because in this correction equation, a change of the current Ip2 due to a decrease of an oxygen amount caused by a clogging of the fourth diffusion control part 45 is calculated and sensitivity degradation of the gas sensor 100 due to other causes is not included in the correction coefficient K. Nevertheless, the characteristics line L2' is found that affection of the sensitivity degradation is drastically compensated, compared to the characteristics line L2.

The sensitivity degradation of the gas sensor 100 changes according to an usage situation of each gas sensor. Thus, it is possible to make a correction on the basis of a lot of data in order to make a correction on the basis of experimental data, but errors are inevitably observed.

On the other hand, the correction method described above calculates the correction coefficient K on the basis of a theoretical correction equation, using an output based on oxygen concentration controlled with high accuracy, thereby allowing a stable correction. The sensitivity degradation caused by a clogging of the fourth diffusion control part 45 is a main cause of the sensitivity degradation, so that it is possible to make a correction to take in a most part of a change of a sensor output due to the sensitivity degradation with stable accuracy.

As described above, even when it is not easy to measure the relation of NO concentration and the current Ip2 of the gas sensor 100 after the sensitivity degradation, it is possible to correct a change of a sensor output due to the sensitivity degradation caused by contaminants clogging in the fourth diffusion control part 45 by making the above correction.

<Second Correction Method>

Next, a method (second correction method) for correcting an output similarly to the first correction method will be described. In this method, a difference value for the gas sensor 100 for a target of a correction (a correction target gas sensor) obtained in the first correction method (in the step S3 in FIG. 5) by the following equation:

$$\Delta IpC(=IpC-IpCo) \quad (13)$$

is calculated with a reference sensor without degradation (that is, a sensor in an initial state), which includes the same structure as the correction target gas sensor 100, but is a different sensor from the actually-used sensor 100.

The present invention focuses on a temporal change of measurement characteristics for oxygen concentration as an indicator of a degradation state of a gas sensor. Thus, it is necessary to gain information that how a state of oxygen measurement characteristics of the gas sensor for the target of a correction was in the initial state. Processes to specify the oxygen measurement characteristics correspond to the steps S1 to S3 in FIG. 5, but the second correction method described here is based on a principle that the oxygen measurement characteristics in the initial state can be estimated only if the NOx measurement characteristics in the initial state is found out, even though measurement characteristics of oxygen concentration was not measured when the correction target sensor 100 was in the initial state.

That is, in the second correction method, a part of the first correction method is changed, and the relation of oxygen concentration and the sensor output Ip2 when the actually-used sensor for the target of a correction was in the initial state, is presumably calculated from characteristics of the reference sensor.

In the case of considering sensitivity degradation of the gas sensor 100 caused by a clogging of a porous body forming the fourth diffusion control part 45, actual target for the measurement is $O_2$ even in measuring NO concentration, so that a change rate of the current Ip2 to a change of NO concentration in the case of measuring NO concentration and a change rate of the current Ip2 to a change of $O_2$ concentration in the case of measuring $O_2$ concentration are slightly different in the identical gas sensor 100, but those change rates are kept substantially same, i.e. gradients are almost same, as long as reduction of NO is performed stably.

Here, the same gas sensor is not used here for the reference sensor and the correction target sensor, but those sensors are manufactured in the same manufacturing process so that those are assumed to behave similarly.

From the above, the ratio of the current Ip2 between measuring NOx and $O_2$ is obtained by the measurement with the actually-used correction target sensor and that with the reference sensor in the initial state, respectively. The output correction value for the correction target sensor is calculated based thereon.

Figure 7:
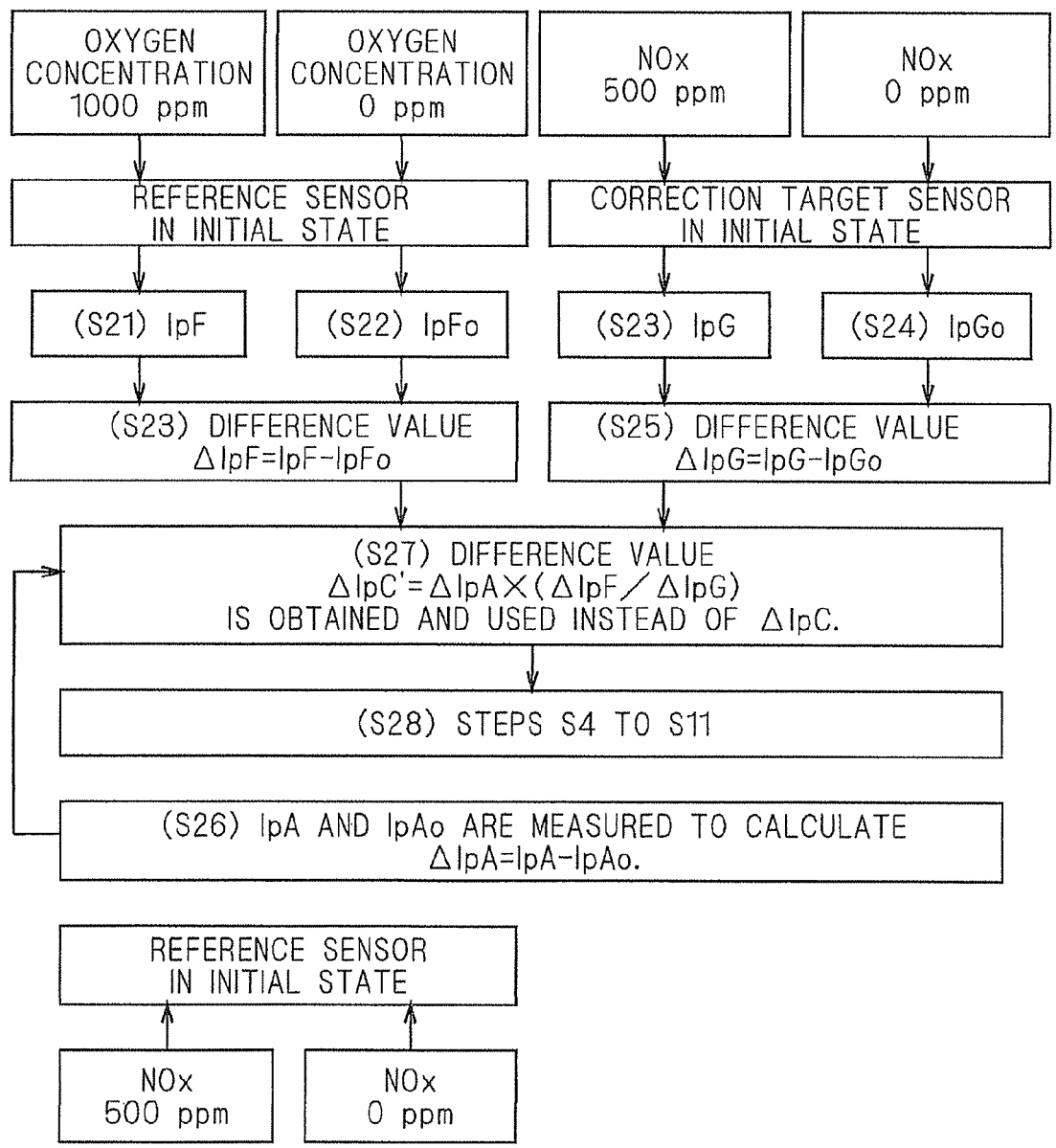
FIG. 7 is a view for showing a flow of a second correction method.

FIG. 7 is a view for showing a flow of the second correction method. The sensor output IpF under the condition that oxygen concentration is 1000 ppm and the sensor output IpFo under the condition that oxygen concentration is 0 ppm are measured with respect to the reference sensor in the initial state (step S21 and step S22). Alternatively, previously measured values are prepared.

The sensor output IpG under the condition that NOx concentration is 500 ppm and the sensor output IpGo under the condition that NOx concentration is 0 ppm are measured with respect to the correction target sensor in the initial state (step S23 and step S24). Alternatively, previously measured values are prepared.

The sensor output IpA under the condition that NOx concentration is 500 ppm and the sensor output IpAo under the condition that NOx concentration is 0 ppm are previously measured with respect to the reference sensor in the initial state (see FIG. 3), and a difference thereof is calculated by the following equation (step S26).

$$\Delta IpA = IpA - IpAo \quad (14)$$

These values are used for calculating the following equation.

$$\Delta IpC' = \Delta IpA \times (\Delta IpF/\Delta IpG) \quad (15)$$

Then, the above equation is used instead of the following equation (step S27):

$$\Delta IpC = IpC - IpCo \quad (16)$$

which corresponds to the change of oxygen concentration from 0 ppm to 1000 ppm in the initial state of the gas sensor 100 for the target of a correction.

That is, the difference value $\Delta IpC$ (or change rate P0) is a value characterizing detection characteristics of the correction target sensor for oxygen concentration in the initial state. However, even if the detection characteristics for oxygen concentration has not been measured, a data value $\Delta IpC'$ which approximately provides the difference value $\Delta IpC$ can be obtained by calculating a ratio ($\Delta IpF/\Delta IpG$) representing the relation of detection characteristics between NOx concentration and oxygen concentration in the initial state, only if getting: a) the change rate P1 of the sensor output with respect to oxygen concentration, represented by detection characteristics parameters IpF and IpFo of the reference sensor for oxygen concentration in the initial state; b) the change rate Q1 of the sensor output with respect to NOx concentration, represented by detection characteristics parameters IpF and IpFo of the reference sensor for NOx concentration in the initial state; and c) the change rate Q0 of the sensor output with respect to NOx concentration, represented by a value $\Delta IpA$ characterizing detection characteristics of the correction target sensor for NOx concentration in the initial state.

If represented by a change rate, the change rate P0 characterizing the detection characteristics of the correction target sensor for oxygen concentration in the initial state is obtained by the following equation.

$$P0 = P1 \times (Q0/Q1) \quad (17)$$

The value $\Delta IpC$ approximated by the data value $\Delta IpC'$ in the step S27 as described above is used instead of the value $\Delta IpC$ obtained in the steps S1 to S3 of the first correction method to perform the subsequent steps S4 to S11, thereby calculating a current IpE, which represents the current Ip2 after the correction of the sensor output, by correcting after-degraded output value IpB similarly to the first correction method (a step S28).

<Correction by Experimental Data>

The above-described first and second correction methods correct a change of a sensor output due to sensitivity degradation caused by contaminants such as Na, Mg, Ca or the like clogging in the fourth diffusion control part 45, which has been confirmed to be a main cause of the sensitivity degradation by the inventors.

With respect to the sensitivity degradation not directly caused by contaminants clogging in the fourth diffusion control part 45, a correction based on experimental data or the like may be performed with. For instance, it is possible to make a correction on the basis of the result obtained from the relation of NO concentration and the current Ip2 in the initial state and after sensitivity degradation, the relation of oxygen concentration and the current Ip2, and further the relation between those values and other sensor outputs (the pump current Ip0 and the pump current Ip1), for a number of the gas sensors 100.

Specifically, a difference between oxygen output characteristics and NOx concentration dependency of a sensor output is previously specified based on experimental data, as a value of a correction factor g, and the sensor output Qc after the correction in the above is further corrected by multiplying the value of the correction factor g. Then, sensor output Qc' is corrected twice like the following equation: Qc'=g×Qc. As illustrated in FIG. 6, when a correction by a proportional calculation is weak, the value of the correction factor g is greater than 1.

As a result, a change of a sensor output caused by a clogging of the fourth diffusion control part 45 which is a main cause of the sensitivity degradation is corrected with stable accuracy on the basis of a theoretical equation, and in addition to this, on the basis of data of experiments and the actually-used gas sensor, allowing to approach a sensor output of the gas sensor 100 in the initial state.

<Variation>

The correction performed by the correction methods described in the present embodiment is not implemented only in the gas sensor 100, but may be implemented as a correction of a sensor output of the gas sensor 100 in a gas sensing system including an ECU (engine control unit) which is a microcontroller for comprehensively performing an electronic control in an operation of an automobile engine or the like. In this case, the control of the correction of the sensor output may be implemented in the gas sensor 100 or in the ECU.

EXAMPLE

As an example, sensor output of the gas sensor 100 after degradation was corrected by the second correction method, using another gas sensor 100 without degradation therewith.

First, a value of the sensor output Ip2 under the condition that a voltage of 400 mV was applied between the outside pump electrode 23 and the measuring electrode 44 was measured. The value of the sensor output Ip2 on measuring $N_2$ concentration was 0.51 μA. The value of the sensor output Ip2 under the condition that NO concentration was 2000 ppm was 6.31 μA, and the value of the sensor output Ip2 under the condition that oxygen concentration was 1000 ppm was 4.87 μA.

The first value of them is subtracted from the second and third value of them, respectively. The former resultant value of 5.80 μA corresponds to an amount of a change of the sensor output Ip2 when NO concentration changes by 2000 ppm. Since the value of the sensor output Ip2 for the change of NO concentration is proportional, the amount of the change of the sensor output Ip2 when NO concentration changes by 500 ppm is 1.450 μA.

Similarly, the latter resultant value about the above subtraction is 4.36 μA. Since there is a proportional relation between oxygen concentration and the sensor output Ip2, the sensor output Ip2 changes by 1.09 μA when oxygen concentration changes by 250 ppm. From the above, the ratio of the amount of the change of the sensor output Ip2 when NO concentration changes from 0 ppm to 500 ppm to the amount of the change of the sensor output Ip2 when oxygen concentration changes from 0 ppm to 250 ppm is 1.450:1.090. Those values in the above are shown in Table 1.

TABLE 1

| | Ip2 (μA) | | | ΔIp2 (μA) | |
|---|---|---|---|---|---|
| | $N_2$ | NO (2000 ppm) | $O_2$ (1000 ppm) | NO (500 ppm) | $O_2$ (250 ppm) |
| Gas Sensor Before Degradation | 0.51 | 6.31 | 4.87 | 1.450 | 1.090 |
| Gas Sensor After Degradation | 0.33 | | 4.05 | | 0.930 |

TABLE 2

| | Initial Ip2 (μA) | Ip2 After Degradation (μA) |
|---|---|---|
| Gas Sensor After Degradation | 1.655 | 1.011 |

Table 2 shows the initial sensor output Ip2 and the sensor output Ip2 after degradation of the degraded gas sensor as an output difference between the condition that NO concentration is 500 ppm and the condition that NO concentration is 0 ppm. The value of the initial sensor output Ip2 was 1.655 μA, and the value of the sensor output Ip2 after degradation was 1.011 μA.

If the value of the initial sensor output Ip2 of the degraded gas sensor 100 under the condition that oxygen concentration is 250 ppm is shown as x, it can be expressed as 1.655: x=1.450:1.090, using the above-described ratio of the gas sensor 100 before degradation. From the above equation, a value of x is 1.244. As a result, the initial sensor output Ip2 with respect to the oxygen concentration was calculated.

Subsequently, the sensor output Ip2 when a voltage applied between the outside pump electrode 23 and the measuring electrode 44 described above is 400 mV was measured. The current Ip2 on measuring $N_2$ was 0.33 μA. The value of the sensor output Ip2 under the condition that oxygen concentration was 1000 ppm was 4.05 μA. The former value of 0.33 μA of them is subtracted from the latter value of them, and the subtracted value is divided by 4, thereby to obtain a value of 0.930 μA.

From the above, the initial sensor output Ip2 (1.244 μA) and the sensor output Ip2 (0.930 μA) after the sensitivity degradation of the degraded gas sensor 100 with respect to oxygen concentration of 250 ppm are obtained.

Subsequently, the correction coefficient was actually calculated by these values. Specifically, as described in the first correction method, a value of 1.344 μA is obtained by multiplying a value of 1.655 μA by a value of (1.09/1.45) corresponding to the correction coefficient K.

Accordingly, the sensor output Ip2 of the gas sensor 100 after the sensitivity degradation under the condition that NO concentration is 500 ppm is corrected from 1.011 μA to 1.344 μA. From the above, the value after the correction has been confirmed to approach the actual initial value of 1.655 μA.

Figure 8:
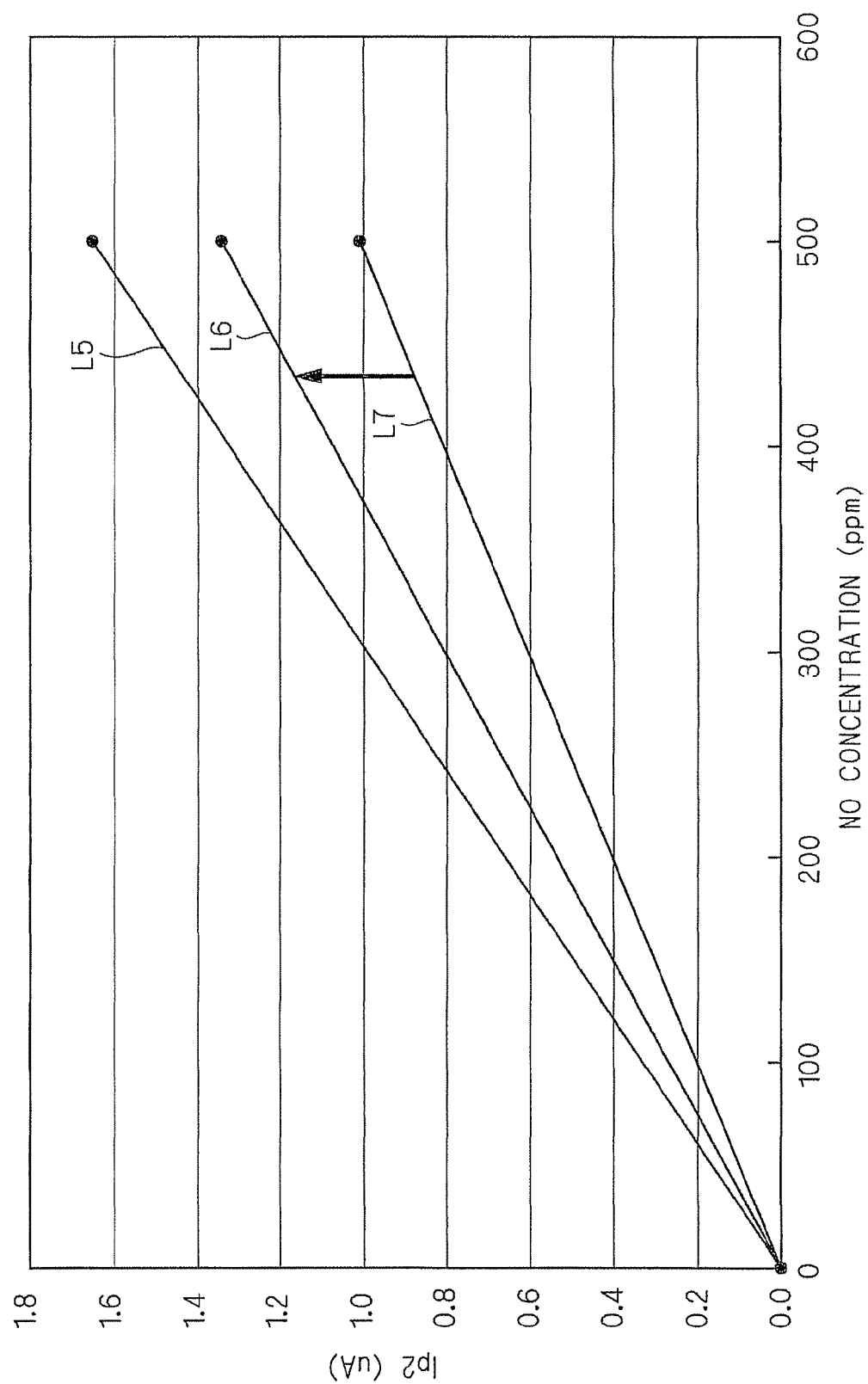
FIG. 8 is a view for showing a relation of NO concentration and the current Ip2 in the initial gas sensor 100, the gas sensor 100 after the sensitivity degradation and the gas sensor 100 after a correction of a sensor output.

FIG. 8 is a view for showing the relation of NO concentration and the sensor output Ip2 of a gas sensor after a correction in the example. A characteristics line L5 shows the relation of NO concentration and the sensor output Ip2 of the gas sensor 100 without degradation, a characteristics line L6 shows the relation of NO concentration and the sensor output Ip2 of the gas sensor 100 after degradation, and a characteristics line L7 shows the corrected sensor output Ip2 of the gas sensor 100 after degradation. As shown in FIG. 8, output deterioration has been considerably improved by correcting deterioration of the sensor output Ip2 caused by a clogging of the fourth diffusion control part 45 on the basis of a theoretical equation.

What is claimed is:

1. a gas sensor for measuring NOx concentration in a measurement gas, comprising:
   (a) a sensor element including
      an oxygen control part arranged and adapted to control oxygen concentration in the measurement gas, and
      a measuring part arranged and adapted to measure NOx concentration by detecting an amount of oxygen in the measurement gas while generating oxygen by resolving NOx in the measurement gas after being passed through said oxygen control part; and
   (b) a control device for controlling said sensor element including
      a detection element arranged and adapted to detect current oxygen output characteristics in said sensor element, and
      a correction element arranged and adapted to correct a change rate of sensor output with respect to detection of NOx in the measurement gas by determining a difference between the current oxygen output characteristics of the sensor element and initial oxygen output characteristics of the sensor element or a reference sensor element to determine an effect of sensor degradation on the current oxygen output characteristics, and correcting said change rate of sensor output with respect to detection of NOx in accordance with the difference between the initial oxygen output characteristics and the current oxygen output characteristics of the sensor element;
   wherein said oxygen output characteristics are relationships between said sensor output and said oxygen concentration,
   wherein said correction element is arranged and adapted to correct a change rate of Q of sensor output with respect to a change of NOx concentration on the basis of a change rate P and a change rate P0, said change rate P being a change rate of sensor output with respect to a change of oxygen concentration and representing said current oxygen output characteristics, and said change rate P0 being a change rate of sensor output with respect to the change of oxygen concentration and representing said initial oxygen output characteristics, and
   wherein said correction element is arranged and adapted to obtain a change rate Qc on the basis of a proportional calculation: Qc=(P/P0)×Q, said change rate Qc being a change rate after said change rate Q is corrected.

2. The gas sensor according to claim 1, wherein
said initial oxygen output characteristics P0 is determined by an actual measurement of said sensor element in its initial state.

3. The gas sensor according to claim 1, wherein
said change rate P0 is calculated on the basis of a proportional calculation: P0=P1×(Q0/Q1), P1 being a change rate of sensor output with respect to the change of oxygen concentration of a reference sensor element in an initial state, said reference sensor element being a different sensor element having the same structure as said sensor element, Q1 being a change rate of sensor output with respect to the change of NOx concentration of said reference sensor element in an initial state, and Q0 being a change rate of sensor output with respect to the change of NOx concentration of a sensor element in an initial state which is the object of a correction.

4. The gas sensor according to claim 1, wherein
a difference between oxygen output characteristics and a NOx concentration dependency of said sensor output is previously specified as a value of a correction factor on the basis of experimental data, and
said correction element further corrects said change rate Qc by said correction factor.

5. A gas sensor control device for controlling a sensor element, said sensor element including a oxygen control part arranged and adapted to control oxygen concentration in a measurement gas, and a measuring part arranged and adapted to measure NOx concentration by detecting an amount of oxygen in the measurement gas while generating oxygen by resolving NOx in the measurement gas after being passed through said oxygen control part, the gas sensor control device comprising:
   a detection element arranged and adapted to detect current oxygen output characteristics in said sensor element; and
   a correction element arranged and adapted to correct a change rate of sensor output with respect to detection of NOx in the measurement gas by determining a difference between the current oxygen output characteristics of the sensor element and initial oxygen output characteristics of the sensor element or a reference sensor element to determine an effect of sensor degradation on the current oxygen output characteristics, and correcting said change rate of sensor output with respect to detection of NOx in accordance with the difference between the initial oxygen output characteristics and the current oxygen output characteristics of the sensor element;
   wherein said oxygen output characteristics are relationships between said sensor output and said oxygen concentration,
   wherein said correction element is arranged and adapted to correct a change rate Q of sensor output with respect to a change of NOx concentration on the basis of a change rate P and a change rate P0, said change rate P being a change rate of sensor output with respect to a change of oxygen concentration and representing said current oxygen output characteristics, and said change rate P0 being a change rate of sensor output with respect to the change of oxygen concentration and representing said initial oxygen output characteristics, and
   wherein said correction element is arranged and adapted to obtain a change rate Qc on the basis of a proportional calculation: Qc=(P/P0)×Q, said change rate Qc being a change rate after said change rate Q is corrected.

6. The gas sensor control device according to claim 5, wherein
said gas sensor control device is provided to be accompanied by said sensor element.

7. The gas sensor control device according to claim 5, wherein
said gas sensor control device is assembled into an engine control unit separately from said sensor element.

8. A method of measuring NOx concentration in a measurement gas by a sensor element, said sensor element including an oxygen control part for controlling oxygen concentration in the measurement gas, and a measuring part for measuring NOx concentration by detecting an amount of oxygen in the measurement gas while generating oxygen by resolving NOx in the measurement gas after being passed through said oxygen control part, the method comprising the steps of:

(a) detecting current oxygen output characteristics in said sensor element, and
(b) correcting a change rate of sensor output with respect to detection of NOx in the measurement gas in accordance with a difference between initial oxygen output characteristics and said current oxygen output characteristics in said sensor element,
wherein said oxygen output characteristics are relationships between said sensor output and said oxygen concentration,
wherein a correction element is arranged and adapted to correct a change rate Q of sensor output with respect to a change or NOx concentration on the basis of a change rate P and a change rate P0, said change rate P being a change rate of sensor output with respect to a change of oxygen concentration and representing said current oxygen output characteristics, and said change rate P0 being a change rate of sensor output with respect to the change of oxygen concentration and representing said initial oxygen output characteristics, and
wherein said correction element is arranged and adapted to obtain a change rate Qc on the basis of a proportional calculation: $Qc=(P/P0) \times Q$, said change rate Qc being a change rate after said change rate Q is corrected.

* * * * *